US012337190B2

(12) United States Patent
Ota (10) Patent No.: US 12,337,190 B2
(45) Date of Patent: Jun. 24, 2025

(54) ENDOSCOPE SYSTEM AND PHOTOTHERAPY METHOD HAVING A CORRECTION OPERATION WHEN AN OBSERVATION MODE IS SET TO A THERMAL SUPPRESSION MODE

(71) Applicant: OLYMPUS MEDICAL SYSTEMS CORP., Tokyo (JP)

(72) Inventor: Chikashi Ota, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 449 days.

(21) Appl. No.: 17/938,402

(22) Filed: Oct. 6, 2022

(65) Prior Publication Data

US 2024/0115874 A1 Apr. 11, 2024

(51) Int. Cl.
*A61N 5/06* (2006.01)
*A61B 1/00* (2006.01)
*A61B 1/06* (2006.01)

(52) U.S. Cl.
CPC .......... *A61N 5/062* (2013.01); *A61B 1/00009* (2013.01); *A61B 1/0638* (2013.01); *A61B 1/0684* (2013.01); *A61N 2005/0662* (2013.01)

(58) Field of Classification Search
None
See application file for complete search history.

(56) References Cited

U.S. PATENT DOCUMENTS

| | | | |
|---|---|---|---|
| 2002/0123666 A1* | 9/2002 | Matsumoto | A61B 1/0669 600/178 |
| 2005/0234302 A1* | 10/2005 | MacKinnon | A61B 1/043 600/109 |
| 2005/0251230 A1* | 11/2005 | MacKinnon | A61B 1/0638 607/92 |
| 2006/0241496 A1* | 10/2006 | Fengler | A61B 1/0638 600/476 |
| 2008/0027280 A1* | 1/2008 | Fengler | A61B 1/05 600/181 |
| 2008/0058602 A1 | 3/2008 | Landry | |
| 2008/0278592 A1* | 11/2008 | Kuno | H04N 25/134 348/E9.002 |
| 2010/0073731 A1* | 3/2010 | Takei | A61B 1/00096 358/475 |
| 2010/0145416 A1* | 6/2010 | Kang | A61N 5/062 607/90 |
| 2012/0163015 A1* | 6/2012 | Hanano | A61B 1/07 362/311.01 |

(Continued)

Primary Examiner — John P Leubecker
(74) *Attorney, Agent, or Firm* — Scully, Scott, Murphy & Presser, P.C.

(57) ABSTRACT

An endoscope system includes: a light source configured to emit white light having wavelength distribution of white color; an optical element configured to block at least light emitted from the light source, the at least light having wavelength band corresponding to a light absorption band with a highest peak from among light absorption bands of a medicinal substance used in phototherapy; an imaging element configured to perform imaging based on a light component which has passed through the optical element; and an image processor configured to process imaging signal obtained as a result of imaging performed by the imaging element, and generate an image.

3 Claims, 7 Drawing Sheets

(56) References Cited

U.S. PATENT DOCUMENTS

| | | | |
|---|---|---|---|
| 2012/0242859 A1* | 9/2012 | Sasaki | A61B 1/0669 |
| | | | 348/E9.051 |
| 2018/0064321 A1* | 3/2018 | Muramatsu | A61B 1/0655 |
| 2018/0153408 A1* | 6/2018 | Yao | A61B 5/0075 |
| 2020/0330785 A1* | 10/2020 | Yoshida | A61B 1/0607 |
| 2022/0021807 A1* | 1/2022 | Weise | A61B 1/043 |
| 2023/0190085 A1* | 6/2023 | Tanaka | G02B 19/0061 |
| | | | 607/88 |
| 2023/0200634 A1* | 6/2023 | Ouyang | A61B 1/0625 |
| | | | 600/476 |
| 2024/0280490 A1* | 8/2024 | Perry | G02B 21/0032 |

* cited by examiner

ENDOSCOPE SYSTEM AND PHOTOTHERAPY METHOD HAVING A CORRECTION OPERATION WHEN AN OBSERVATION MODE IS SET TO A THERMAL SUPPRESSION MODE

TECHNICAL FIELD

The disclosure relates to an endoscope system and a phototherapy method.

BACKGROUND

In recent years, the research is underway regarding photoimmunotherapy (PIT) for cancer treatment in which an antibody conjugate is bound specifically with the protein substance of cancer cells, and infrared light representing the treatment light is applied for activating the antibody conjugate and destroying the cancer cells. The antibody conjugate that is irradiated with the infrared light causes swelling of the cancer cells and induces their death. At that time, as a result of becoming excited, the antibody conjugate produces fluorescence. The intensity of the fluorescence is used as an index for the efficacy of treatment.

Meanwhile, with the aim of observing the treatment site, a white light is applied to the treatment site. However, the antibody conjugate reacts to the light components included in the white light, more particularly, reacts to the elements by which the antibody conjugate becomes excited, causing the unexpected side effects and thermal reactions due to the high absorption coefficient of IRdye700 of the antibody drug conjugate. These reactions lead to a risk of causing a higher level of thermal burn to the tissues than intended. In order to resolve that issue, a technology is known in which the surface temperature is detected using a temperature sensor and the amount of illumination light is accordingly controlled (for example, refer to US Patent Application Laid-Open No. 2008/0058602).

However, if the amount of illumination light is controlled in the manner disclosed in Patent Literature 1, then there occurs a drop in the amount of illumination light during the treatment, thereby making the observation region dark. Thus, there is a trade-off between the risk of a thermal burn attributed to the treatment and the brightness of the observation region.

It could therefore be helpful to provide an endoscope system and a phototherapy method that enable reducing the risk of a thermal burn attributed to the treatment as well as securing the brightness of the observation region.

SUMMARY

In some embodiments, an endoscope system includes: a light source configured to emit white light having wavelength distribution of white color; an optical element configured to block at least light emitted from the light source, the at least light having wavelength band corresponding to a light absorption band with a highest peak from among light absorption bands of a medicinal substance used in phototherapy; an imaging element configured to perform imaging based on a light component which has passed through the optical element; and an image processor configured to process imaging signal obtained as a result of imaging performed by the imaging element, and generate an image.

In some embodiments, a phototherapy method includes: inserting an endoscope into a region including target site for treatment; administering a medicinal substance, which is used in phototherapy, to the target site for treatment; setting an observation mode to a thermal invasion suppression mode in which illumination light is emitted, the illumination light being light in which at least light having wavelength band corresponding to a light absorption band with a highest peak from among light absorption bands of the medicinal substance is blocked; generating that includes performing imaging based on the illumination light and generating an image; and performing treatment by irradiating the target site for treatment with treatment light that causes the medicinal substance to react.

According to the disclosure, it becomes possible to reduce the risk of a thermal burn attributed to the treatment as well as to secure the brightness of the observation region.

DETAILED DESCRIPTION

An illustrative embodiment (hereinafter, called "embodiment") is described below. In the embodiment, as an example of an endoscope system, the explanation is given about a medical endoscope system using which images of the inside of the body of the subject, such as a patient, are taken and displayed, and an optical immunotherapy method is implemented. However, the disclosure is not limited by the embodiment. Moreover, in the explanation of the drawings, the same constituent elements are referred to by the same reference numerals.

Embodiment

Figure 1:
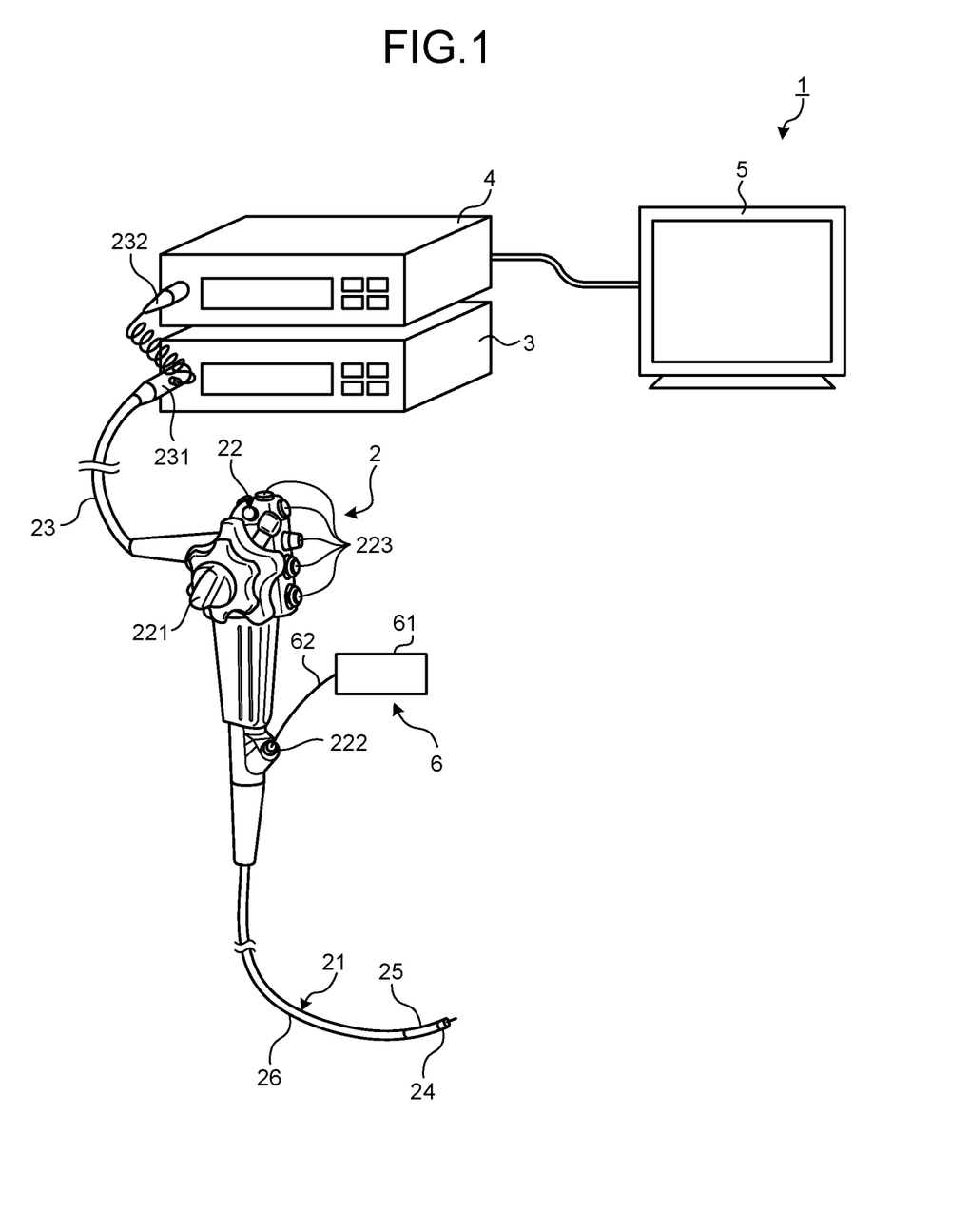
FIG. 1 is a diagram illustrating an overall configuration of an endoscope system according to an embodiment of the disclosure.
Figure 2:
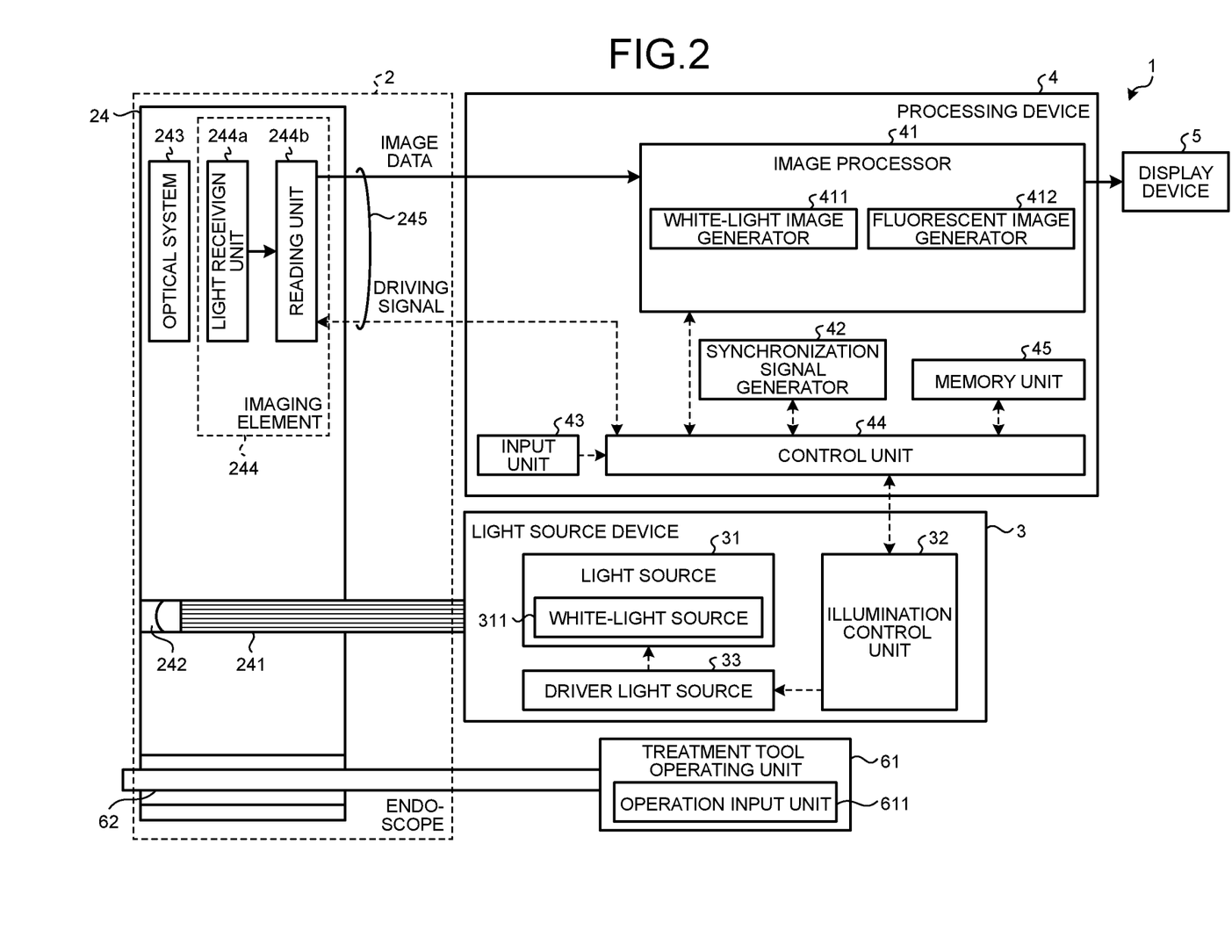
FIG. 2 is a block diagram illustrating an overall configuration of the endoscope system.
Figure 3:
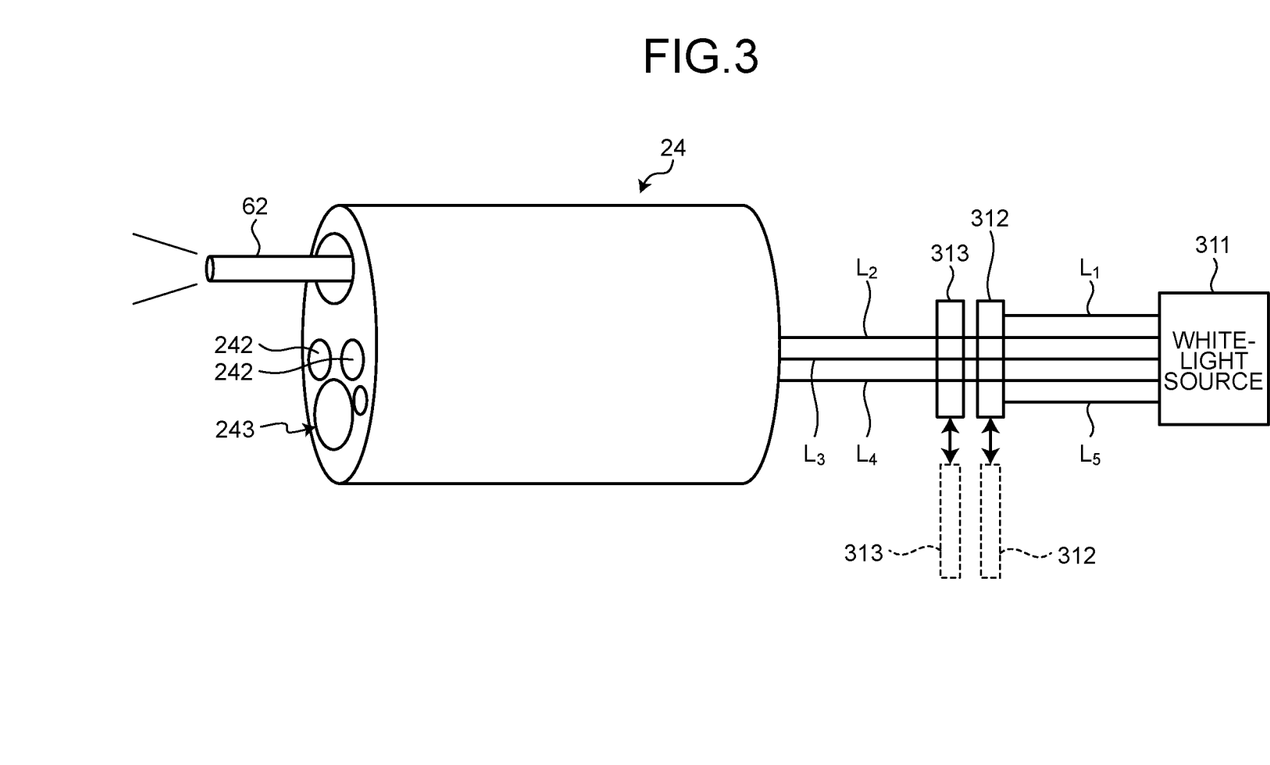
FIG. 3 is a diagram for explaining a front-end configuration of an endoscope according to the embodiment.

FIG. 1 is a diagram illustrating an overall configuration of the endoscope system according to the embodiment of the disclosure. FIG. 2 is a block diagram illustrating an overall configuration of the endoscope system according to the present embodiment. FIG. 3 is a diagram for explaining a front-end configuration of the endoscope according to the present embodiment.

The endoscope system 1 illustrated in FIGS. 1 and 2 includes the following: an endoscope 2 that, when the front end portion thereof is inserted into the body of the subject, takes in-vivo images of the subject; a light source device 3 that generates an illumination light to be emitted from the front end of the endoscope 2; a processing device 4 that performs predetermined signal processing with respect to imaging signals which are obtained by the endoscope 2 by performing imaging and that comprehensively controls the overall operations of the endoscope system 1; a display device 5 that displays in-vivo images which are generated as a result of the signal processing performed by the processing device 4.

The endoscope 2 includes the following: a flexible and elongated insertion portion 21; an operating unit 22 that is connected to the proximal end of the insertion portion 21 and that receives input of various operation signals; and a universal cord 23 that extends from the operating unit 22 in the opposite direction to the direction of extension of the insertion portion 21, and that has various built-in cables connected to the light source device 3 and the processing device 4.

The insertion portion 21 includes the following: a front end portion 24 that has a built-in imaging element 244 in which pixels meant for receiving light and generating signals according to photoelectric conversion are arranged in a two-dimensional manner; a freely-bendable curved portion 25 that is made of a plurality of bent pieces; and a flexible tube 26 that is a flexible and long tube connected to the proximal end of the curved portion 25. The insertion portion 21 is inserted into the body cavity of the subject. Then, using the imaging element 244, the insertion portion 21 takes images of the body tissue present at such positions inside the subject up to which the outside light does not reach.

The operating unit 22 includes the following: a bending knob 221 that makes the curved portion 25 bend in the vertical direction and the horizontal direction; a treatment tool insertion portion 222 through which a treatment tool such as a treatment-light application device, biopsy forceps, an electrical scalpel, or an inspection probe is inserted into the body cavity of the subject; and a plurality of switches 223 representing operation input units that receive input of operation instruction signals regarding the peripheral devices including not only the processing device 4 but also an insufflation unit, a water supply unit, and a screen display control. The treatment tool inserted from the treatment tool insertion portion 222 passes through a treatment tool channel (not illustrated) in the front end portion 24 and comes out from an opening (not illustrated) of the front end portion 24 (see FIG. 3).

The universal cord 23 at least has a built-in light guide 241 and a built-in cable assembly 245, which has one or more cables bundled therein. The universal cord 23 is branched at the end portion on the opposite side to the side of connection with the operating unit 22. At the branched end portion of the universal cord 23, a connector 231 is disposed that is detachably attachable to the light source device 3, and a connector 232 is disposed that is detachably attachable to the processing device 4. From the end portion of the connector 231, some part of the light guide 241 extends out. The universal cord 23 propagates the illumination light, which is emitted from the light source device 3, to the front end portion 24 via the connector 231 (the light guide 241), the operating unit 22, and the flexible tube 26. Moreover, the universal cord 23 transmits the image signals, which are obtained as a result of the imaging performed by the imaging element 244 that is disposed in the front end portion 24, to the processing device 4 via the connector 232. The cable assembly 245 includes a signal line for transmitting imaging signals; a signal line for transmitting driving signals meant for driving the imaging element 244; and a signal line for sending and receiving information such as the specific information related to the endoscope 2 (the imaging element 244). In the embodiment, the explanation is given under the premise that a signal line is used for transmitting electrical signals. Alternatively, a signal line can be used for transmitting optical signals, or can be used for transmitting signals between the endoscope 2 and the processing device 4 in a wireless manner.

The front end portion 24 is made of fiberglass, and includes the following: the light guide 241 that constitutes a light guiding path for the light generated by the light source device 3; an illumination lens 242 that is disposed at the front end of the light guide 241; an optical system 243 that collects light; and the imaging element 244 that is disposed at the image formation position of the optical system 243 and that receives the light collected by the optical system 243, performs photoelectric conversion, and performs predetermined signal processing with respect to electrical signals.

The optical system 243 is configured using one or more lenses. The optical system 243 forms an observation image on the light receiving surface of the imaging element 244. Meanwhile, the optical system 243 can also be equipped with the optical zooming function meant for varying the angle of view and the focusing function meant for varying the focal point.

The imaging element 244 performs photoelectric conversion with respect to the light coming from the optical system 243, and generates electrical signals (imaging signals). In the imaging element 244, a plurality of pixels, each of which includes a photodiode for storing the electrical charge according to the amount of light and includes a capacitor for converting the electrical charge transferred from the photodiode into a voltage level, is arranged as a two-dimensional matrix. In the imaging element 244, each pixel performs photoelectric conversion with respect to the incoming light coming via the optical system 243 and generates an electrical signal. Then, the imaging element 244 sequentially reads the electrical signals generated by arbitrarily-set target pixels for reading from among a plurality of pixels, and outputs those electrical signals as imaging signals. The imaging element 244 is configured using, for example, a CCD image sensor (CCD stands for Charge Coupled Device) or a CMOS image sensor (CMOS stands for Complementary Metal Oxide Semiconductor).

Meanwhile, the endoscope 2 also includes a memory (not illustrated) that is used to store: an execution program that enables the imaging element 244 to execute various operations; a control program; and data containing the identification information of the endoscope 2. The identification information contains specific information (ID) of the endoscope 2, the model year of the endoscope 2, the specifications of the endoscope 2, and the transmission method. Moreover, the memory can also be used to temporarily store the image data that is generated by the imaging element 244.

According to the present embodiment, in the endoscope system 1, one of the following modes is set as the observation mode: a normal observation mode for observing images that are obtained as a result of the illumination of the white light; a fluorescent observation mode for observing fluorescent images that are obtained as a result of the illumination of the treatment light; and a thermal invasion suppression mode for holding down the thermal invasion with respect to the tissues during the observation performed using the white light.

Given below is the explanation of a configuration of the light source device 3. The light source device 3 includes a light source 31, an illumination control unit 32, and a light source driver 33. The light source 31 emits the illumination light under the control of the illumination control unit 32.

The light source 31 is configured using a light source and one or more lenses, and emits a light (illumination light) when the light source is driven. The light generated by the light source 31 is emitted toward the subject from the front end of the front end portion 24 via the light guide 241. The light source 31 includes a white-light source 311, a first filter 312, and a second filter 313.

The white-light source 311 emits a light (white light) having the wavelength band of a broad visible range. The white-light source 311 is implemented using an LED light source, a laser light source, a xenon lamp, or a halogen lamp.

In the present embodiment, the explanation is given about an example in which the white-light source represents a plurality of light sources emitting lights having mutually different wavelength bands, and the white light is formed by synthesizing the lights generated by those light sources. The white-light source 311 emits a white light that is made of the following lights emitted by the light sources: a light $L_1$ having the wavelength band greater than 650 nm; a light $L_2$ having the wavelength band equal to or greater than 550 nm and equal to or smaller than 650 nm; a light $L_3$ having the wavelength band equal to or greater than 500 nm and smaller than 550 nm; a light $L_4$ having the wavelength band equal to or greater than 450 nm and smaller than 500 nm; and a light $L_5$ having the wavelength band equal to or greater than 380 nm and smaller than 450 nm.

Explained below with reference to FIGS. 4 to 7 are the optical characteristics of the white light, the treatment light, the antibody conjugate, the first filter 312, and the second filter 313. Herein, the explanation is given about an example in which IRDye (registered trademark) 700DX is used as the antibody conjugate.

Figure 4:
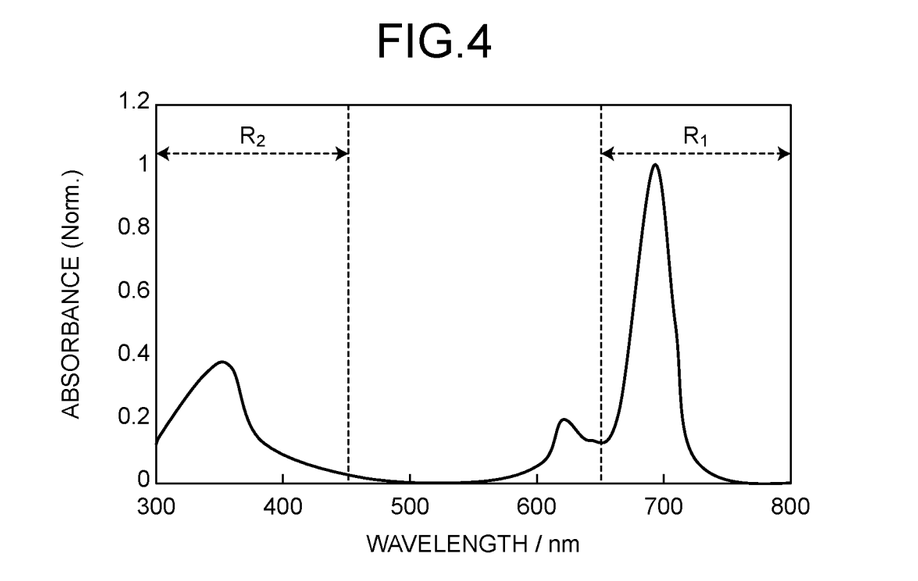
FIG. 4 is a diagram illustrating an absorption spectrum of IRDye (registered trademark) 700DX of an antibody conjugate.

FIG. 4 is a diagram illustrating an absorption spectrum of IRDye (registered trademark) 700DX. In the wavelength band greater than 650 nm, IRDye (registered trademark) 700DX has a light absorption band $R_1$ with the peak of 690 nm. In the wavelength band smaller than 450 nm, IRDye (registered trademark) 700DX has a light absorption band $R_2$ with the peak of 350 nm. During phototherapy, the light absorption band $R_1$ is equivalent to the target wavelength band for causing the antibody conjugate to react. The light absorption band $R_2$ is also called the Soret band.

Figure 5:
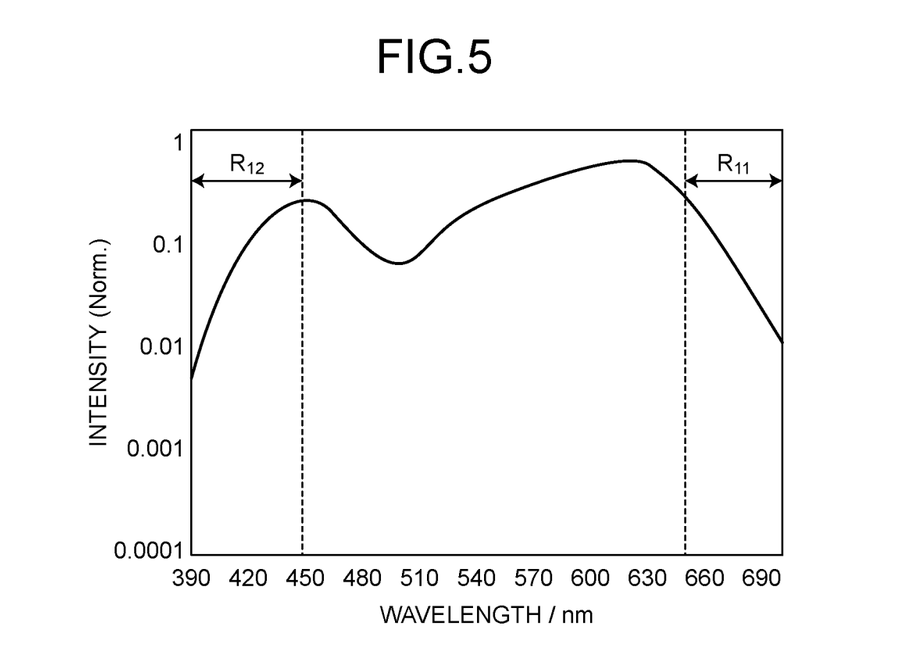
FIG. 5 is a diagram illustrating an example of the wavelength spectrum of the white light emitted by a white-light source.

FIG. 5 is a diagram illustrating an example of the wavelength spectrum of the white light emitted by the white-light source. The white light has, for example, the light intensity distribution illustrated in FIG. 5.

Figure 6:
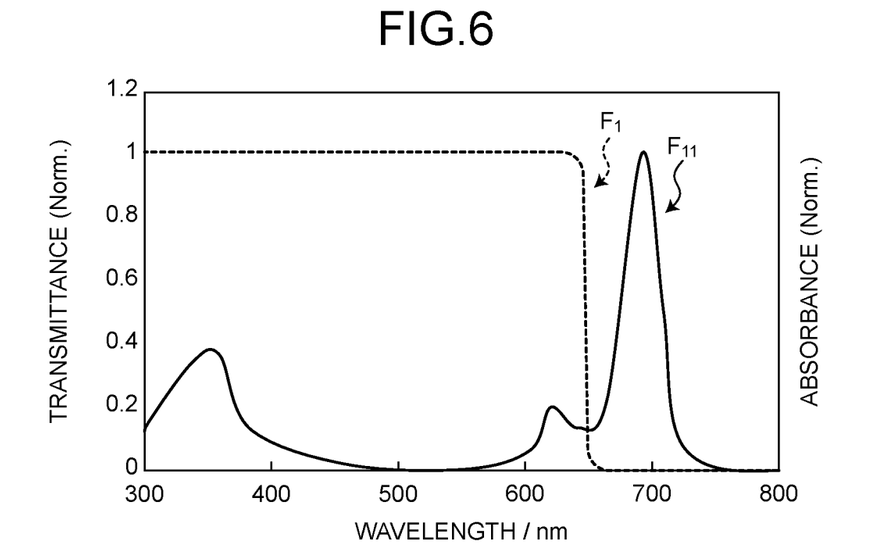
FIG. 6 is a diagram for explaining the characteristics of a first filter.

FIG. 6 is a diagram for explaining the characteristics of the first filter. The first filter 312 has the absorption characteristics illustrated by a curved line $F_1$. That is, the first filter 312 blocks the light having the wavelength band greater than 650 nm, and allows the lights having other wavelength bands (equal to or smaller than 650 nm) to pass through. Meanwhile, a curved line $F_{11}$ indicates the absorption characteristic of IRDye (registered trademark) 700DX (see FIG. 4).

Figure 7:
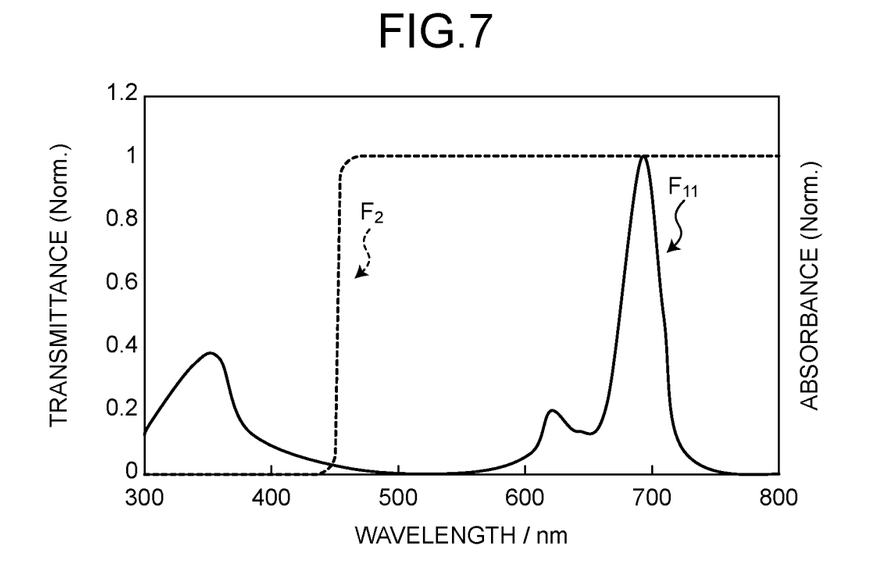
FIG. 7 is a diagram for explaining the characteristics of a second filter.

FIG. 7 is a diagram for explaining the characteristics of the second filter. The second filter 313 has the absorption characteristics illustrated by a curved line $F_2$. That is, the second filter 313 blocks the light having the wavelength band smaller than 450 nm, and allows the lights of other wavelength bands (equal to or greater than 450 nm) to pass through.

When lights are blocked by the first filter 312 and the second filter 313, IRDye (registered trademark) 700DX no more gets irradiated with the lights having the wavelength bands corresponding to the light absorption band. That makes it possible to hold down the thermal invasion of the tissues due to the lights other than the treatment light.

At that time, even if some elements of the white light (the wavelength bands $R_{11}$ and $R_{12}$ illustrated in FIG. 5) are blocked by the first filter 312 and the second filter 313, there is no significant drop in the color balance of the obtained white-light images.

Based on a control signal (a modulated-light signal) received from the processing device 4, the illumination control unit 32 controls the amount of power to be supplied to the light source 31, as well as controls the light sources to be used for generating lights and controls the driving timings of the light sources.

Moreover, the illumination control unit 32 performs insertion and removal of the first filter 312 and the second filter 313 with respect to the light path of the light emitted by the white-light source 311. More particularly, when the normal observation mode is set, the illumination control unit 32 moves the first filter 312 and the second filter 313 away from the light path of the light emitted by the white-light source 311. When the thermal invasion suppression mode is set, the illumination control unit 32 inserts the first filter 312 and the second filter 313 in the light path of the light emitted by the white-light source 311.

Under the control of the illumination control unit 32, the light source driver 33 supplies an electric current to the light sources to be used for emitting lights, and thus makes the light source 31 emit a light.

Given below is the explanation of a configuration of the processing device 4. The processing device 4 includes an image processor 41, a synchronization signal generator 42, an input unit 43, a control unit 44, and a memory unit 45.

The image processor 41 receives imaging signals that are obtained by the imaging element 244 by performing imaging and that include the image data of the illumination light of each color. Moreover, if analog image data is received from the endoscope 2, then the image processor 41 performs A/D conversion and generates digital signals. Furthermore, if image data is received in the form of light signals from the endoscope 2, then the image processor 41 performs photoelectric conversion and generates digital image data. Subsequently, the image processor 41 processes the received imaging signals, and generates images to be displayed in the display device 5.

The image processor 41 performs predetermined image processing with respect to the image data received from the endoscope 2; generates images; and outputs them to the display device 5. Moreover, the image processor 41 sets a reinforcement region determined based on the images. Furthermore, the image processor 41 calculates the time variation of the fluorescence intensity. The image processor 41 includes a white-light image generator 411 and a fluorescent image generator 412.

The white-light image generator 411 generates a white-light image based on an image formed due to the white light.

The fluorescent image generator 412 generates a fluorescent image based on an image formed due to the fluorescence. For example, the fluorescence is generated when the treatment light is emitted and the antibody conjugate becomes excited.

The white-light image generator 411 and the fluorescent image generator 412 generate images by performing predetermined image processing. Herein, predetermined image processing includes synchronization, gray level correction, and color correction. The synchronization is performed to synchronize the image data of the RGB color components. The gray level correction is performed to correct the gray level of the image data. The color correction is performed to correct the color tone of the image data. Meanwhile, the white-light image generator 411 and the fluorescent image generator 412 can also perform gain adjustment according to the brightness of the images.

The white-light image generator 411 and the fluorescent image generator 412 perform operations according to the observation mode that is set. For example, when the normal observation mode or the thermal invasion suppression mode is set, the white-light image generator 411 performs the operations. On the other hand, when the fluorescent observation mode is set, the fluorescent image generator 412 performs the operations. However, in each observation mode, both image generators can perform the operations.

The image processor 41 is configured using a general-purpose processor such as a central processing unit (CPU), or a dedicated processor such as an arithmetic circuit represented by an application specific integrated circuit (ASIC) that implements specific functions. Meanwhile, the image processor 41 can be configured to include a frame memory for holding R image data, G image data, and B image data.

The synchronization signal generator 42 generates a clock signal (a synchronization signal) serving as the basis for the operations of the processing device 4, and outputs the synchronization signal to the light source device 3, the image processor 41, the control unit 44, and the endoscope 2. Herein, the synchronization signal generated by the synchronization signal generator 42 includes a horizontal synchronization signal and a vertical synchronization signal.

Thus, the light source device 3, the image processor 41, the control unit 44, and the endoscope 2 perform operations in synchronization due to the generated synchronization signal.

The input unit 43 is implemented using a keyboard, a mouse, switches, or a touch-sensitive panel, and receives input of various signals such as an operation instruction signal meant for instructing the operations of the endoscope system 1. Meanwhile, the input unit 43 can also include switches disposed in the operating unit 22, or can include an external portable terminal such as a tablet computer.

The control unit 44 performs driving control of all constituent elements including the imaging element 244 and the light source device 3, and performs input-output control of information with respect to each constituent element. The control unit 44 refers to control information data (for example, the reading timing) that is to be used in imaging control and that is stored in the memory unit 45, and sends a driving signal to the imaging element 244 via a predetermined signal line included in the cable assembly 245. Moreover, the control unit 44 sets the observation mode, and switches among the observation modes. For example, based on an operation input performed by the operator, the control unit 44 sets the normal observation mode, the fluorescent observation mode, or the thermal invasion suppression mode. The control unit 44 is configured using a general-purpose processor such as a CPU or a dedicated processor such as an arithmetic circuit represented by an ASIC that implements specific functions.

The memory unit 45 is used to store various computer programs meant for operating the endoscope system 1, and to store data containing various parameters required for the operations of the endoscope system 1. Moreover, the memory unit 45 is used to store the identification information of the processing device 4. The identification information contains the specific information (ID) of the processing device 4, the model year of the processing device 4, and the specifications of the processing device 4.

Furthermore, the memory unit 45 is used to store various computer programs including an image obtaining program meant for executing an image obtaining method implemented in the processing device 4. The computer programs can be widely distributed by recording them in a computer-readable recording medium such as a hard disk, a flash memory, a CD-ROM, a DVD-ROM, or a flexible disk. Alternatively, the computer programs can be downloaded via a communication network. The communication network is implemented using, for example, a known public line network, or a local area network (LAN), or a wide area network (WAN); and can be of the wired type or the wireless type.

The memory unit 45 having the abovementioned configuration is implemented using a read only memory (ROM) in which various computer programs are installed in advance and using a RAM or a hard disk in which operation parameters and data of various operations are stored.

The display device 5 displays images that correspond to the image signals received from the processing device 4 (the image processor 41) via a video cable. The display device 5 is configured using a monitor such as a liquid crystal display or an organic electro luminescence (EL) display.

A treatment device 6 includes a treatment tool operating unit 61, and includes a flexible treatment tool 62 that extends from the treatment tool operating unit 61. The treatment tool 62 that is used in PIT represents a treatment-light emitting unit that emits a light for enabling treatment (hereinafter, called the treatment light). The treatment tool operating unit 61 controls the emission of the treatment light from the treatment tool 62. The treatment tool operating unit 61 includes an operation input unit 611. The operation input unit 611 is configured using, for example, switches. In response to an input (for example, in response to the pressing of a switch) of the operation input unit 611, the treatment tool operating unit 61 makes the treatment tool 62 emit the treatment light. Meanwhile, in the treatment device 6, the light source that emits the treat light can be installed in the treatment tool 62 or can be installed in the treatment tool operating unit 61. The light source is implemented using a semiconductor laser or an LED. For example, in the case of PIT, the treatment light has the wavelength band equal to or greater than 680 nm and, for example, has the central wavelength of 690 nm.

Herein, the illumination optical system included in the treatment tool 62 can be configured to change the application range of the treatment light. For example, under the control of the treatment tool operating unit 61, the illumination optical system can be configured using an optical system in which the focal distance can be varied or using a digital micromirror device (DMD); and it is possible to vary the spot diameter of the light with which the subject is irradiated and to vary the shape of the application range.

Figure 8:
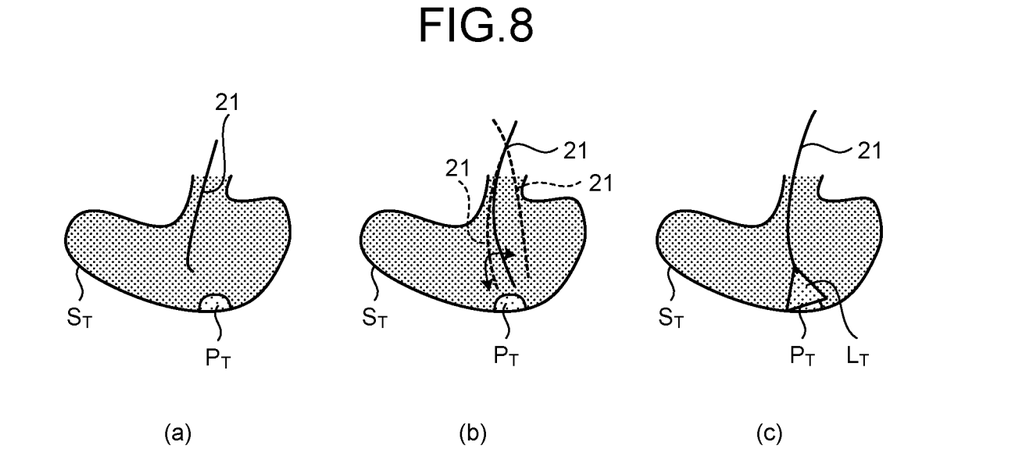
FIG. 8 is a diagram illustrating an exemplary flow of the treatment performed using the endoscope.

Explained below with reference to FIG. 8 is the flow of the treatment performed using the endoscope 2. FIG. 8 is a diagram illustrating an exemplary flow of the treatment performed using the endoscope according to the embodiment of the disclosure. In FIG. 8 is illustrated an example of implementing PIT; and the insertion portion 21 is inserted into a stomach $S_T$, which represents the region including the target site for treatment, for carrying out the treatment of a target site $P_T$.

Firstly, the operator inserts the insertion portion 21 into the stomach $S_T$ (see (a) in FIG. 8). The observation mode is set to the normal observation mode, and the operator instructs the light source device 3 to emit the white light and searches for the treatment position (the target site $P_T$) while observing the white-light image that captures the inside of the stomach $S_T$ and that is displayed in the display device 5.

Once the target site $P_T$ is confirmed, an antibody conjugate is administered to the target site $P_T$. The antibody conjugate can be administered either using the endoscope 2, or using some other device, or by asking the patient to swallow a medicinal substance.

At that time, before or immediately after administering the antibody conjugate, the observation mode is set to the thermal invasion suppression mode. Consequently, some light components of the white light are blocked by the first filter 312 and the second filter 313. Then, while observing the white-light images generated from the illumination light from which the light components having the wavelength bands corresponding to the light absorption band of the antibody conjugate are blocked, the operator adjusts the orientation of the front end portion 24 with respect to the target site $P_T$ (see (b) in FIG. 8). At that time, as a result of blocking the light components of the wavelength bands corresponding to the light absorption band of the antibody conjugate, there is no thermal invasion even if the front end portion 24 and the target site $P_T$ come close to each other.

After adjusting the orientation of the front end portion 24, the operator causes the treatment tool 62 to protrude from the front end of the endoscope 2 and applies the treatment light $L_T$ to the target site $P_T$ (see (c) in FIG. 8). Because of the irradiation with the treatment light, the antibody conjugate bound to the target site $P_T$ reacts and the target site $P_T$ gets treated. During the treatment, the operator changes the thermal invasion suppression mode to the fluorescent observation mode, and observes the fluorescent images to confirm the cumulative dosage of the antibody conjugate and to confirm the efficacy of treatment. For example, the efficacy of treatment is determined by the operator by observing the fluorescent images for the fluorescence intensity and the fluorescence distribution.

As may be necessary, the operator applies additional treatment light and confirms the efficacy of treatment in a repeated manner.

Figure 9:
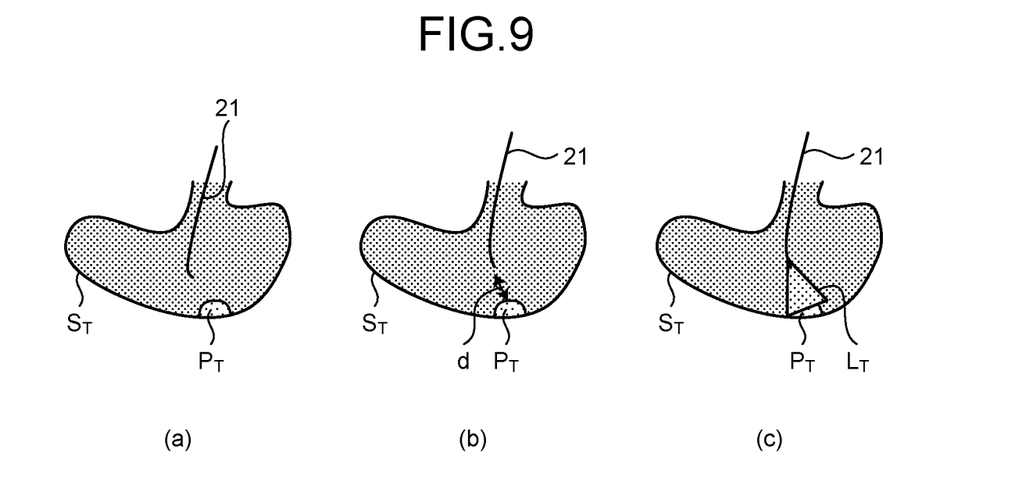
FIG. 9 is a diagram illustrating an exemplary flow of the conventional treatment.

Explained below with reference to FIG. 9 is the flow of the conventional treatment. FIG. 9 is a diagram illustrating an exemplary flow of the conventional treatment. In an identical manner to FIG. 8, in FIG. 9 is illustrated an example of implementing PIT; and the insertion portion 21 is inserted into the stomach $S_T$ for carrying out the treatment of the target site $P_T$.

Firstly, the operator inserts the insertion portion 21 into the stomach $S_T$ (see (a) in FIG. 9). At that time, the observation mode is set to the normal observation mode, and the operator instructs the light source device 3 to emit the white light and searches for the treatment position (the target site $P_T$) while observing the white-light image that captures the inside of the stomach $S_T$ and that is displayed in the display device 5. Once the target site $P_T$ is confirmed, an antibody conjugate is administered to the target site $P_T$. The antibody conjugate can be administered either using the endoscope 2, or using some other device, or by asking the patient to swallow a medicinal substance.

After administering the antibody conjugate, the normal observation mode is still maintained as the observation mode. Then, while observing a white-light image that is generated due to the illumination light from which the light components having the wavelength bands corresponding to the light absorption band of the antibody conjugate are not blocked, the operator adjusts the orientation of the front end portion 24 with respect to the target site $P_T$ (see (b) in FIG. 9). At that time, if the front end portion 24 moves too close to the target site $P_T$, then there is an increase in the intensity of the white light applied to the target site $P_T$ to which the antibody conjugate is bound. When the white light is applied to the target site $P_T$ to which the antibody conjugate is bound, the antibody conjugate becomes excited due to the light components of the light absorption band included in the white light. The excited antibody conjugate produces heat due to which the target site $P_T$ or the surrounding tissues are exposed to the risk of a thermal invasion. On the other hand, in order to avoid excessive application of the white light, if the observation is carried out by maintaining a sufficiently long distance d between the front end portion 24 and the target site $P_T$, then it becomes difficult to observe the target site $P_T$ and it also requires efforts to secure the distance d.

After the orientation of the front end portion 24 is adjusted, the operator causes the treatment tool 62 to protrude from the front end of the endoscope 2 and the treatment light $L_T$ to the target site $P_T$ (see (c) in FIG. 9). During the period of time in which the treatment light is applied, the operator switches between the normal observation mode and the fluorescent observation mode, and confirms the efficacy of treatment while observing the fluorescent images. However, due to the normal observation mode, sometimes the reaction (excitation) of the antibody conjugate keeps on advancing.

In the embodiment described above, during the observation of the target site after the administration of an antibody conjugate; from among the light components of the white light, the light components having the wavelength bands corresponding to the light absorption band of the antibody conjugate are blocked using the first filter 312 and the second filter 313. As a result of blocking the light components having such wavelength bands, the reaction of the antibody conjugate is held down at the time of observation. As a result, at times other than during treatment, the thermal invasion attributed to the antibody conjugate can be held down. Moreover, since the blocked wavelength bands have only a small impact on white-light images, it becomes possible to generate white-light images in which a decline in color reproducibility is held down. Thus, according to the present embodiment, it becomes possible to reduce the risk of a thermal burn attributed to the treatment as well as to secure the brightness of the observation region.

Meanwhile, in the present embodiment, the first filter 312 and the second filter 313 can be fixedly disposed in the optical path on a constant basis. In that case, in the normal observation mode too, white-light images are generated without using the light components that have been blocked by the first filter 312 and the second filter 313; so that the manner of observation becomes same as in the thermal invasion suppression mode. Hence, the observation is always performed with a reduced level of thermal invasion.

First Modification Example

Figure 10:
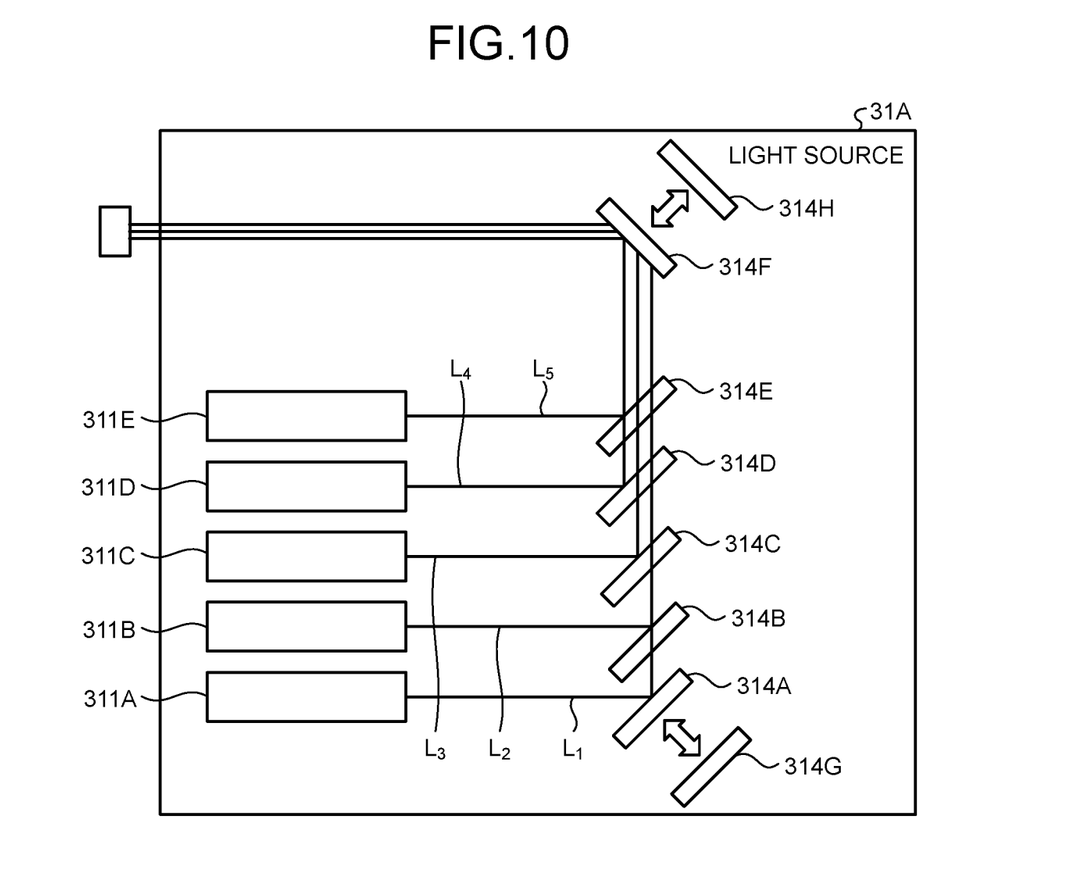
FIG. 10 is a diagram for explaining a configuration of a white-light source according to a first modification example.

Given below is the explanation of a first modification example of the embodiment. An endoscope system according to the first modification example includes a light source 31A in place of the light source 31 of the endoscope system 1 according to the embodiment. The remaining configuration is identical to the configuration according to the embodiment. Hence, that explanation is not given again. In the first modification example, the light source device does not include the first filter 312 and the second filter 313. Thus, in the first modification example, the light emitted from the light source 31A falls on the light guide 241.

The flow of operations in the present endoscope system is identical to the flow of operations according to the embodiment.

FIG. 10 is a diagram for explaining a configuration of the white-light source according to the first modification example. The light source 31A includes: a plurality of LED light sources (a first light source 311A, a second light source 311B, a third light source 311C, a fourth light source 311D, and a fifth light source 311E); a plurality of reflection filters (a first reflection filter 314A, a second reflection filter 314B, a third reflection filter 314C, a fourth reflection filter 314D, a fifth reflection filter 314E, and a sixth reflection filter 314F); and switch filters (a first switch filter 314G and a second switch filter 314H).

The first light source 311A emits the light $L_1$ having the wavelength band greater than 650 nm.

The second light source 311B emits the light $L_2$ having the wavelength band equal to or greater than 550 nm and equal to or smaller than 650 nm.

The third light source 311C emits the light $L_3$ having the wavelength band equal to or greater than 500 nm and smaller than 550 nm.

The fourth light source 311D emits the light $L_4$ having the wavelength band equal to or greater than 450 nm and smaller than 500 nm.

The fifth light source 311E emits the light $L_5$ having the wavelength band equal to or greater than 380 nm and smaller than 450 nm.

As a result of combining the lights emitted by the light sources, a white light is generated that, for example, has the intensity distribution illustrated in FIG. 5. Meanwhile, each light source is not limited to be configured using an LED light source, can be alternatively configured using a light source in which the wavelength band of the emitting light can be set.

The first reflection filter 314A reflects the light having all wavelength bands.

The second reflection filter 314B reflects the light having the wavelength band equal to or smaller than 650 nm, and allows the light having the wavelength band greater than 650 nm to pass through.

The third reflection filter 314C reflects the light having the wavelength band smaller than 550 nm, and allows the light having the wavelength band equal to or greater than 550 nm to pass through.

The fourth reflection filter 314D reflects the light having the wavelength band smaller than 500 nm, and allows the light having the wavelength band equal to or greater than 500 nm to pass through.

The fifth reflection filter 314E reflects the light having the wavelength band smaller than 450 nm, and allows the light having the wavelength band equal to or greater than 450 nm to pass through.

The sixth reflection filter 314F is disposed in the optical path of the light that has been bent by the first reflection filter 314A to the fifth reflection filter 314E, and bends the incident light toward the exit opening of the light source 31A. Thus, the light bent by the first reflection filter 314A to the fifth reflection filter 314E falls on the sixth reflection filter 314E.

The first switch filter 314G reflects the light having the frequency band equal to or smaller than 650 nm, and allows the light having the frequency band greater than 650 nm to pass through. The first switch filter 314G is disposed in such a way that it can be switched with the first reflection filter 314A in the optical path of the first light source 311A. When the normal observation mode is set, the illumination control unit 32 places the first reflection filter 314A in the optical path. When the thermal invasion suppression mode is set, the illumination control unit 32 places the first switch filter 314G in the optical path.

The second switch filter 314H reflects the light having the frequency band equal to or greater than 450 nm, and allows the light having the frequency band smaller than 450 nm to pass through. The second switch filter 314H is disposed in such a way that it can be switched with the sixth reflection filter 314F. When the normal observation mode is set, the illumination control unit 32 places the sixth reflection filter 314F in the optical path. When the thermal invasion suppression mode is set, the illumination control unit 32 places the second switch filter 314H in the optical path.

In the normal observation mode, the first reflection filter 314A and the sixth reflection filter 314F are disposed. The lights of all frequency bands emitted from the first light source 311A to the fifth light source 311E fall on the sixth reflection filter 314F and are bent toward the exiting opening of the light source 31A. That is, in the normal observation mode, the lights of all frequency bands emitted from the first light source 311A to the fifth light source 311E get emitted from the light source 31A.

On the other hand, in the thermal invasion suppression mode, the first switch filter 314G and the second switch filter 314H are placed, and the light having the wavelength band equal to or greater than 450 nm and equal to or smaller than 650 nm falls on the second switch filter 314H and gets bent toward the exiting opening of the light source 31A. That is, in the thermal invasion suppression mode, the light having the wavelength band greater than 650 and the light having the wavelength band smaller than 450 nm are excluded, and the light having the wavelength band equal to or greater than 450 nm and equal to or smaller than 650 nm is emitted from the light source 31A.

In the first modification example explained above, during the observation of the target site after the administration of an antibody conjugate, the first switch filter 314G and the second switch filter 314H are placed so that, from among the light components of the white light, the light components corresponding to the light absorption band of the antibody conjugate are blocked. As a result of blocking the light components of such wavelength bands, the reaction of the antibody conjugate is held down at the time of observation. As a result, at times other than during treatment, the thermal invasion attributed to the side effects of the antibody conjugate can be held down. Moreover, since the blocked wavelength bands have only a small impact on white-light images, it becomes possible to generate white-light images in which a decline in color reproducibility is held down. Thus, according to the first modification example, it becomes possible to reduce the risk of a thermal burn attributed to the treatment as well as to secure the brightness of the observation region.

Meanwhile, in the first modification example, the first switch filter 314G and the second switch filter 314H can be fixedly disposed in the optical path on a constant basis. In that case, in the normal observation mode too, white-light images are generated without using the light components that have been blocked by the first switch filter 314G and the second switch filter 314H; so that the manner of observation becomes same as in the thermal invasion suppression mode. Hence, the observation is always performed with a reduced level of thermal burn.

Second Modification Example

Given below is the explanation of a second modification example of the embodiment. An endoscope system according to the second modification example is identical to the endoscope system 1 according to the embodiment. Hence, that explanation is not given again. However, in the second modification example, some of the operations performed by the image processor 41 are different than the operations in the embodiment. The following explanation is given about the operations that are different than the operations in the embodiment.

In the second modification example, in the thermal invasion suppression mode in which the color components are blocked by the first filter 312 and the second filter 313, the white-light image generator 411 performs correction such as white balance adjustment in order to correct the color reproducibility. For example, when the thermal invasion suppression mode is set, the R signal value decreases due to the first filter 312, and the B signal value decreases due to the second filter 313. For that reason, with the aim of compensating for the signal values of the blocked color components, the white-light image generator 411 performs correction such as varying the correction coefficients in such a way that the RGB ratio becomes equal to the RGB ratio during the normal observation, increasing the gain of the signal values of the color components close to the concerned color components, and interpolating the blocked color components.

The setting regarding execution/nonexecution of such correction can be appropriately changed in the setting of the thermal invasion suppression mode.

In the second modification example explained above, it becomes possible to achieve the same effect as achieved in the embodiment. Moreover, in the thermal invasion suppression mode, it becomes possible to enhance the color reproducibility of the white-light images.

In the embodiment and the modification examples explained above, as long as at least the wavelength bands that are on the side of the light absorption band having the highest peak of the antibody conjugate are blocked, it becomes possible to achieve the effect explained above. That is, in the case of the antibody conjugate mentioned above (IRDye (registered trademark) 700DX), if the first filter 312 or the first switch filter 314G is disposed for at least blocking the light components having the wavelength band greater than 650 nm, then it becomes possible to achieve the effect.

Meanwhile, as an example of the antibody conjugate, the explanation is given about an antibody conjugate used in PIT. Alternatively, the antibody conjugate can be a medicinal substance used in other optical treatment such as photodynamic therapy (PDT).

In the embodiment described above, the light source device 3 is installed as a separate device from the processing device 4. Alternatively, the light source device 3 and the processing device 4 can be configured in an integrated manner. Moreover, in the embodiment, the explanation is given about using a treatment tool for emitting the treatment light. Alternatively, the light source device 3 can be configured to emit the treatment light.

Furthermore, in the embodiment described above, the explanation is given about the case in which the endoscope system according to the disclosure is the endoscope system 1 in which the flexible endoscope 2 is used that treats the body tissue of the subject as the observation target. Alternatively, the endoscope system according to the disclosure can be an endoscope system in which a rigid endoscope is used, or an industrial endoscope is used for observing the characteristics of materials, or a fiberscope is used, or a device is used that is formed by connecting a camera head to the eye piece of an optical endoscope such as an optical visual tube.

As explained above, the endoscope system and the phototherapy method according to the disclosure are suitable in reducing the risk of a thermal burn attributed to the treatment as well as are suitable in securing the brightness of the observation region.

The invention claimed is:

1. An endoscope system comprising:
    a light source configured to emit white light having wavelength distribution of white color;
    an optical element configured to block at least light emitted from the light source, the at least light having a wavelength band corresponding to a light absorption band with a highest peak from among light absorption bands of a medicinal substance used in phototherapy;
    an imaging element configured to perform imaging based on a light component which has passed through the optical element; and
    an image processor configured to process an imaging signal obtained as a result of imaging performed by the imaging element, and generate an image;
    wherein the image processor is configured to perform a correction operation to correct a light component that is blocked by the optical element;
    as an observation mode of the light source, either a normal observation mode in which a subject is irradiated with the white light is set, or a thermal invasion suppression mode in which a subject is irradiated with illumination light that has passed through the optical element is set, and
    when the thermal invasion suppression mode is set, the image processor is configured to perform the correction operation.

2. The endoscope system according to claim 1, wherein the optical element includes at least either one of
    a first filter configured to block light having wavelength band greater than 650 nm and allow light having wavelength band equal to or smaller than 650 nm to pass through, and
    a second filter configured to block light having wavelength band smaller than 450 nm and allow light having wavelength band equal to or greater than 450 nm to pass through.

3. A phototherapy method comprising:
    inserting an endoscope into a region including target site for treatment;
    administering a medicinal substance, which is used in phototherapy, to the target site for treatment;
    setting an observation mode to either a normal observation mode in which a subject is irradiated with the white light, or a thermal invasion suppression mode in which illumination light is emitted, the illumination light being light in which at least light having a wavelength band corresponding to a light absorption band with a highest peak from among light absorption bands of the medicinal substance is blocked;
    performing imaging based on the illumination light and generating an image;
    performing treatment by irradiating the target site for treatment with treatment light that causes the medicinal substance to react; and performing a correction operation to correct a light component that is blocked when the thermal invasion suppression mode is set.

* * * * *